(12) United States Patent
Hauer et al.

(10) Patent No.: US 10,932,386 B2
(45) Date of Patent: Feb. 23, 2021

(54) ELECTRONIC MODULE AND METHOD FOR PRODUCING SAME

(71) Applicant: DYCONEX AG, Bassersdorf (CH)

(72) Inventors: Marc Hauer, Uster (CH); Eckardt Bihler, Winterthur (CH); Jochen Held, Arth (CH)

(73) Assignee: DYCONEX AG, Bassersdorf (CH)

( * ) Notice: Subject to any disclaimer, the term of this patent is extended or adjusted under 35 U.S.C. 154(b) by 0 days.

(21) Appl. No.: 15/993,935

(22) Filed: May 31, 2018

(65) Prior Publication Data

US 2018/0359874 A1 Dec. 13, 2018

(30) Foreign Application Priority Data

Jun. 8, 2017 (EP) .................... 17174971

(51) Int. Cl.
*H05K 5/06* (2006.01)
*H01L 23/00* (2006.01)
(Continued)

(52) U.S. Cl.
CPC .......... *H05K 5/065* (2013.01); *A61N 1/3752* (2013.01); *H01L 23/4985* (2013.01); *H01L 23/49811* (2013.01); *H01L 24/24* (2013.01); *H01L 24/81* (2013.01); *H01L 24/82* (2013.01); *H01L 24/92* (2013.01); *H05K 1/028* (2013.01); *H05K 1/0313* (2013.01); *H05K 1/09* (2013.01); *H05K 1/112* (2013.01); *H05K 1/189* (2013.01); *H05K 3/285* (2013.01); *H05K 3/303* (2013.01); *H05K 3/4076* (2013.01); *A61N 1/3754* (2013.01); *H01L 2224/80203* (2013.01);
(Continued)

(58) Field of Classification Search
CPC ............ A61N 1/3752; H01L 23/49811; H01L 23/4985; H01L 24/24; H01L 24/81; H05K 5/065
USPC ........................................................ 361/751
See application file for complete search history.

(56) References Cited

U.S. PATENT DOCUMENTS 6,306,680 B1 10/2001 Fillion et al.
2003/0111742 A1 6/2003 Iwasaki et al.
(Continued)

FOREIGN PATENT DOCUMENTS

EP 2469591 A2 6/2012
JP 2010147331 A 7/2010

OTHER PUBLICATIONS

European Search Report and Annex to the European Search Report on European Patent Application No. EP 17 17 4971.6, dated Nov. 29, 2017 (7 pages).
(Continued)

*Primary Examiner* — Tremesha S Willis
(74) *Attorney, Agent, or Firm* — Buchanan Ingersoll & Rooney PC

(57) ABSTRACT

An electronic module on a flexible planar circuit substrate with a conductor configuration on a first substrate surface and a plurality of electronic components on the opposite, second substrate surface, wherein the components have component contacts, which are electrically connected selectively by way of vias in the circuit substrate and the conductor configuration, wherein the circuit substrate is a thermoplastic polymer and the component contacts are melted or thermally pressed into the second substrate surface in the region of the vias.

14 Claims, 1 Drawing Sheet

(51) Int. Cl.
*H01L 23/498* (2006.01)
*A61N 1/375* (2006.01)
*H05K 1/02* (2006.01)
*H05K 1/03* (2006.01)
*H05K 1/09* (2006.01)
*H05K 1/11* (2006.01)
*H05K 1/18* (2006.01)
*H05K 3/28* (2006.01)
*H05K 3/30* (2006.01)
*H05K 3/40* (2006.01)

(52) U.S. Cl.
CPC ............ *H01L 2224/80385* (2013.01); *H01L 2224/81191* (2013.01); *H01L 2224/81203* (2013.01); *H01L 2224/81385* (2013.01); *H01L 2224/81898* (2013.01); *H01L 2224/821* (2013.01); *H01L 2224/8236* (2013.01); *H01L 2224/82138* (2013.01); *H01L 2224/82203* (2013.01); *H01L 2224/82895* (2013.01); *H01L 2224/9212* (2013.01); *H01L 2224/92124* (2013.01); *H01L 2224/92144* (2013.01); *H05K 2201/0129* (2013.01); *H05K 2201/0141* (2013.01); *H05K 2201/0154* (2013.01); *H05K 2203/1316* (2013.01); *H05K 2203/1327* (2013.01); *H05K 2203/166* (2013.01)

(56) References Cited

U.S. PATENT DOCUMENTS

| | | | |
|---|---|---|---|
| 2004/0084769 A1* | 5/2004 | Sugaya | H01L 23/49894 257/734 |
| 2006/0049495 A1 | 3/2006 | Hazeyama et al. | |
| 2007/0235810 A1 | 10/2007 | Delgado et al. | |
| 2009/0321118 A1 | 12/2009 | Kim et al. | |
| 2015/0305142 A1* | 10/2015 | Matsuda | H05K 1/024 333/238 |
| 2018/0323170 A1* | 11/2018 | Kim | H01L 25/50 |

OTHER PUBLICATIONS

L. Boettcher et al., "Embedding of Chips for System in Package realization—Technology and Applications", www.izm.fraunhofer.de (7 pages).

European Search Report and Annex to the European Search Report on European Patent Application No. EP 18 174 093.7, dated Nov. 19, 2018 (13 pages).

* cited by examiner

ELECTRONIC MODULE AND METHOD FOR PRODUCING SAME

CROSS-REFERENCE TO RELATED APPLICATIONS

This patent application claims the benefit of and priority to co-pending European Patent Application No. EP 17174971.6, filed on Jun. 8, 2017 in the European Patent Office, which is hereby incorporated by reference in its entirety.

TECHNICAL FIELD

The present invention relates to an electronic module on a flexible planar circuit substrate with a conductor configuration on a first substrate surface and a plurality of electronic components on the opposite, second substrate surface, wherein the components have component contacts, which are electrically connected selectively by way of vias in the circuit substrate and the conductor configuration. The present invention also relates to a method for producing a module of this kind.

BACKGROUND

Electronic modules which are constructed on planar circuit substrates with prefabricated conductor configuration, known as printed circuit boards, have for decades been indispensable in the field of electronics and electrical engineering and are the subject of constant further development.

From the many developments, particular attention has been focused in recent years on what are known as system-in-package (SIP) solutions, and specifically embedded chips or chip-in-polymer arrangements. With regard to the prior art in this specific field, reference is made to L. Boettcher et al. "Embedding of Chips for System in Package realization—Technology and Applications", www.izm.fraunhofer.de, with further literature references. In the case of this technology, standard printed circuit board fittings can be used, as stated in the above publication; however, the use of circuit substrates that consist substantially of a thermoset polymer is also known.

It has been found that standard printed circuit board substrates, particularly in aggressive environments (for example, aggressive atmospheric environments or the body of living beings) are not chemically inert enough and/or have excessively high diffusion rates for oxygen and/or water. The fields of application of the aforesaid technology in conjunction with standard printed circuit boards are therefore limited in this respect, and alternative materials are sought. It is known here that certain thermoplastic polymers have advantageous properties, in particular, in respect of low diffusion rates of oxygen, water and ions; polymers of this kind, however, are not very stable when it comes to thermal lamination in the xy plane. Thus, a person skilled in the art usually does not consider circuit substrate materials of this kind due to the high stability required of the substrate when positioning many microelectronic circuits or other electronic component on an individual substrate.

The present invention is directed at overcoming one or more of the above-mentioned problems.

SUMMARY

An object of the present invention is an improved electronic module that, in particular, can be manufactured with a high positional accuracy of the used components and that is optimized for use in implantable devices and in devices suitable for aggressive environments, and a method for production of said module.

At least this object is achieved in its device aspect by an electronic module having the features of claim 1 and in its method aspect by a method having the features of claim 10. Expedient developments of the inventive concept are the subject of the dependent claims.

The present invention contains a conscious departure from the prevailing belief that thermoplastic polymers are not suitable for mechanical reasons as substrate material of the circuit substrate of electronic modules, and also includes structural and technical aspects by which an electronic module can be realized with use of a circuit substrate of this kind whilst fulfilling all requirements.

The circuit substrate of the electronic module according to the present invention preferably comprises or consists of a (flexible) thermoplastic polymer. An electronic module with such a circuit substrate has a number of advantages compared to electronic modules with circuit substrates made, for example, of thermosetting resins. Such resins are cured during the production process, which leads to chemical bonding of the polymers of the resins to each other. In the cured state, the resin cannot be melted and further components can therefore no longer be melted into the resin. In contrast, an electronic module with a thermoplastic polymer can be further modified by adding further components, since the thermoplastic polymer, unlike the cured resin, can be melted many times over. The electronic modules of the present invention can therefore be used more flexibly as it can be modulated again after the end of the production process.

The component contacts are melted or thermally pressed into the surface of the substrate comprising or consisting of a (flexible) thermoplastic polymer. The melting or thermal pressing of the component contact into the substrate leads to an adjustment of the shape of the surface of the substrate to the shape of the component contact and at the same time to the adherence between the component contact and the substrate.

The thermoplastic polymer of the electronic module is preferably a thermoplastic polymer with a high melting temperature (preferably at least 250° C., more preferably at least 300° C.). Electronic modules made with a substrate that comprises or consists of such a polymer have the advantage that the structure of the electronic module is particularly stable. The different components therefore remain exactly in the same position relative to each other, even during handling of the electronic modules at elevated temperatures. This allows for a very accurate placement of further components on the electronic module. Further components are indeed usually placed on a module relative to already existing features on the module and, in particular, relative to vias (or bores). Since the vias of the electronic module of the present invention are particularly mechanically stable, further components can be placed very accurately on the electronic module. Preferred thermoplastic polymers that allow obtaining this effect are thermoplastic polymers that comprise or consist of LCP, PEEK and/or PEI.

In a particularly preferred embodiment, the thermoplastic polymer of the substrate comprises or consists of LCP. An electronic module with LCP also has the further advantage that it is highly impermeable to water.

The features of the module according to the present invention are to be understood within the sense of the multi-faceted prior art with the broadest possible meaning.

Although the presence of a conductor configuration of this kind on the first substrate surface is essential, a conductor configuration can also be arranged on the second substrate surface, and this also can be configured in the above-mentioned way. Besides the components arranged in accordance with the present invention at least on the second surface of the circuit substrate, components can also be placed similarly on the first substrate surface. In principle, a multi-layered design of the module with a plurality of circuit substrates and paired first and second surfaces and accordingly positioned conductor configurations and component groups is also understood to be comprised within the scope of the present invention.

The vias comprise metallizations realized in apertures of the circuit substrate. The apertures will be referred to hereinafter as "bores", even though they are not produced by means of a boring tool, and although they are not necessarily circular-cylindrical. In embodiments of the present invention, in a prefabricated pattern of apertures or "bores", it can be that only a predetermined number are provided with a metallization in accordance with the component placement plan of the circuit substrate. Embodiments of this kind can be realized with a selective metallization technique (for example by means of a metallization mask). Alternatively, all bores of the bore pattern can also be provided with an inner wall metallization, which simplifies the associated metallization process and makes it less susceptible to faults.

In one embodiment of the present invention, the conductor configuration is formed of a first metallization layer and the vias are formed which a second metallization layer. This means that the basic connection structure is prefabricated on the circuit substrate and the connection between the used components and the basic structure can be produced once the components have been attached to or inserted into the circuit substrate in a subsequent separate step.

In preferred embodiments, the vias have a metallization deposited in bores of the circuit substrate. Here, the deposited metallization can be galvanically reinforced as necessary. In further variants of these embodiments, the vias comprise at least one metal from the group of copper, gold, titanium, tungsten, palladium, chromium, and nickel.

In a further advantageous embodiment, the electronic module is provided at least on the second substrate surface with a thermoplastic protective film encapsulating at least one of the components. This can be made of the same material as the circuit substrate, however, the use of a different thermoplastic material is also possible depending on the application. In embodiments that are currently advantageous, the thermoplastic material or one thermo-plastic material comprises at least one material from the group of liquid-crystal polymer, or LCP; polyether ether ketone, or PEEK; fluorinated polymers, or polyurethanes.

In further embodiments, the circuit substrate has a thickness in the range between 10 µm and 500 µm, in particular between 10 µm and 100 µm. Depending on the size and complexity of the electronic module and the application, however, thinner or thicker substrates can also be considered in principle.

In functions/applications that are currently particularly advantageous, the electronic module is formed as an implantable electromedical implant or module thereof. However, it can also be, in particular, a device or a module of a device that is to be used in "harsh" ambient conditions, in particular in chemically aggressive environments.

A method according to the present invention for producing the above-explained module comprises at least the following steps:

providing the flexible planar circuit substrate comprising a thermoplastic polymer, producing the conductor configuration on the first substrate surface, producing a bore pattern in accordance with the geometry of the conductor configuration, heating the components that are to be placed on the second substrate surface, placing the components, aligned with the bore pattern in the circuit substrate, on the second substrate surface with a predetermined contact pressure and hereby fusing or thermally pressing the component contacts into the second substrate surface in the region of the bore, and depositing metal selectively into the bore pattern and in the surroundings of the bores from the first substrate surface in order to produce the vias.

These steps are also preferably performed in the aforesaid order, although this is not necessary for each step. A conductor configuration is to be understood generally in the sense of a geometric pattern with substantially linear, but also possibly planar conductive coating portions, into which passive functional elements, such as, for example, resistors, inductors and capacitors, can also be inserted.

Furthermore, instead of a heating of the components, a heating of the circuit substrate as such or a combination of the heating both of the components and of the circuit substrate, in each case by suitable means, is also possible in principle in the step used for the fixing of the components in the circuit substrate.

In one embodiment of the present invention, the components are heated to a placement temperature in the range between 100° C. and 400° C., in particular between 250° C. and 350° C., and/or the contact pressure lies in the range between 0.05 N and 50 N, in particular between 0.1 N and 30 N.

In advantageous embodiments of the inventive method, the depositing of metal in the bore pattern is performed following the fusing or thermal pressing-in of the components, in particular, by means of an electrochemical or physical thin-film process, such as, for example, CVD or PVD. Here, conventional, established disconnection methods can be used, provided there is no need for any specific limitations in respect of the thermoplastic substrate material.

Following the metal deposition, a galvanic reinforcement of the deposited thin film is optionally performed. The need to carry out a further method step of this kind (which is also somewhat critical in respect of the process conditions from environmental protection and occupational safety aspects) is a decision that is to be made on the basis of the necessary conductivity and robustness of the conductor configuration or vias.

In an embodiment that is currently preferred, a thermoplastic protective film is laminated on at least a part or parts of the second substrate surface. This lamination can be performed in the same step in which the circuit substrate is equipped with the components, that is to say to some extent the components are pressed into the circuit substrate as the protective film is laminated on. However, a separation of both steps is also possible in principle. Besides the second substrate surface, the first substrate surface, i.e., that having the conductor configuration, can also be covered by a protective film, such that, in particular, a sealing is provided on both sides for optimal protection of the electronic module against ambient influences.

With regard to the method conditions, particularly temperature and contact pressure, the statements provided above normally apply analogously for the step of equipping the circuit substrate with the components; with use of particular lamination films, however, other method parameters can also be set as appropriate.

Further features, aspects, objects, advantages, and possible applications of the present invention will become apparent from a study of the exemplary embodiments and examples described below, in combination with the Figures, and the appended claims

DESCRIPTION OF THE DRAWINGS

Other advantages and expedient features of the present invention follow from the following description of sample embodiments, which make reference to the Figures. The Figures are as follows.

DETAILED DESCRIPTION

Figure 1:
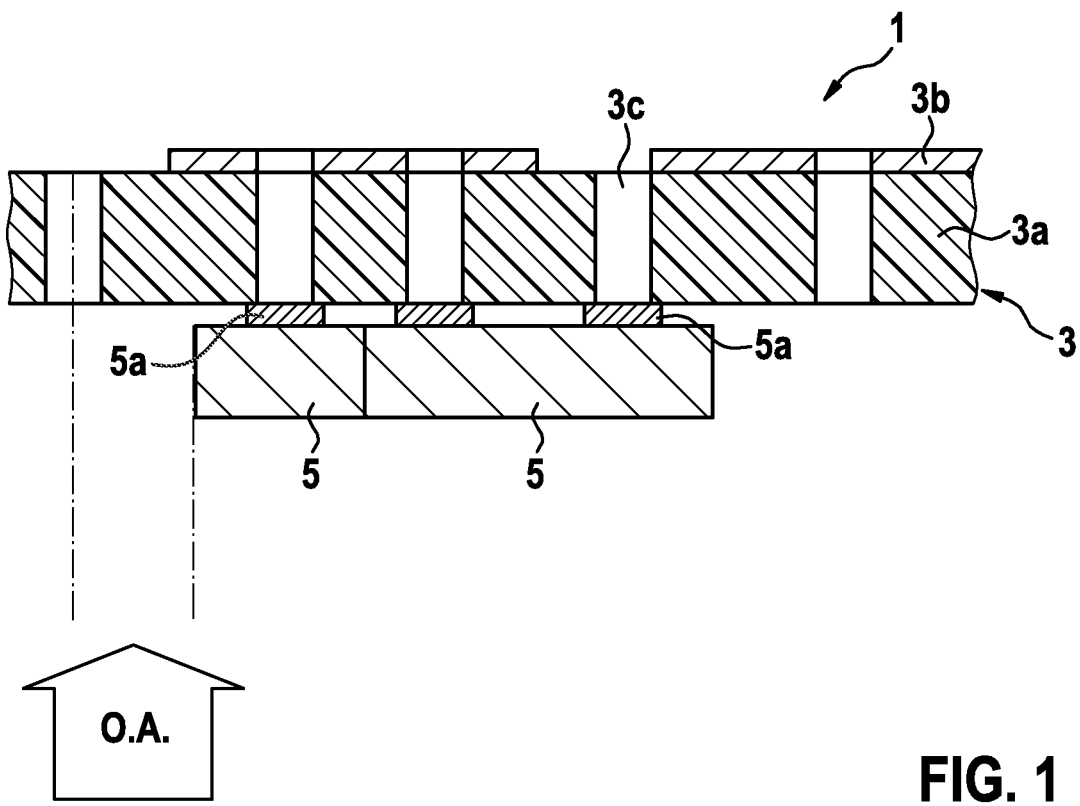
FIG. 1 shows a schematic cross-sectional illustration of an exemplary embodiment of the electronic module according to the present invention during the production process.

FIG. 1 schematically shows a circuit substrate 3 of an (unfinished) electronic module 1, which consists of an LCP (liquid-crystal polymer) film 3a with a conductor configuration 3b coated on one side, together with a plurality of microchips 5, which carries component contacts 5a on a main surface. The microchips 5 are placed on the surface of the flexible planar circuit substrate 3 opposite the conductor configuration 3b, in such a way that the component contacts 5a are aligned with a pattern of bores 3c in the circuit substrate 3.

The alignment between the bore pattern in the circuit substrate 3 and the microchips 5 is achieved by means of an optical alignment process, which is symbolized in FIG. 1 by an arrow with the reference sign O.A. Assembly systems that are typical in this sector, such as, for example, image capture, can be used for this step. Here, the bores 3c in the circuit substrate (the LCP film) are optically recorded and the components are positioned on the circuit substrate with a small positional tolerance (approximately 5-25 μm).

During the positioning, the microchips 5 are heated to a temperature in the vicinity of the Tg of the LCP film 3a, for example, a value in the range between 250° C. and 350° C., and is pressed with a predetermined force, for example, in the range between 0.1 N and 30 N, into the adjacent surface of the LCP film. This is heated locally during this process and thus softens, such that the component contacts 5a are pressed into the adjacent surroundings of the bores 3c and the component adheres flush, without gaps, to the adjacent surface of the circuit substrate 3.

Figure 2:
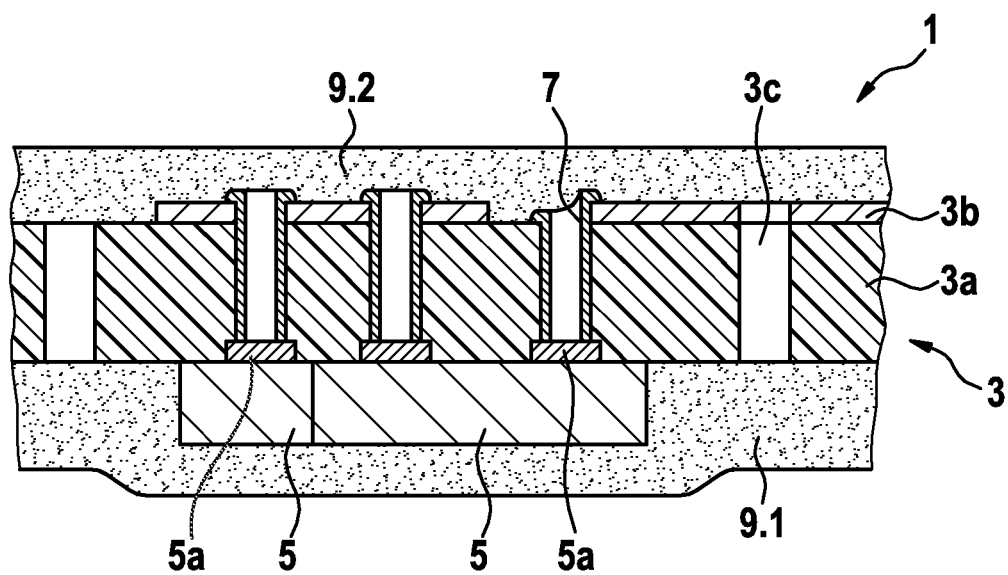
FIG. 2 shows a schematic illustration of the module according to FIG. 1 after manufacture.

FIG. 2 shows the finished state of the module 1, in which the aforementioned adhesion of the microchips 5 to the circuit substrate with components 5a penetrating the surface is provided and can be seen in the figure. Furthermore, a metallization with the surface of the circuit substrate 3 opposite the microchips 5 is in this state performed selectively in those bores 3c in which component contacts 5a are sitting. Vias 7 are hereby formed, which extend as an inner wall metallization of the corresponding bores 3c from the component contacts 5a to the conductor configurations 3b and thus electrically connect the component contacts to the conductor configuration. This inner wall metallization can be produced by an electrochemical or physical thin-film process or also a combination of such processes.

Protective films 9.1 and 9.2 were then laminated one on each of the two surfaces of the circuit substrate 3. The protective films 9.1, 9.2 also consist of a thermoplastic material, for example, an LCP film equivalent to the LCP film 3a. This encapsulates the electronic module 1 in a largely diffusion-tight manner with respect to the surrounding environment, and thus enables use in medical implants or devices for use in harsh environments.

In addition, the present invention can also be embodied in a large number of modifications of the examples shown here and aspects of the present invention detailed further above.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. An electronic module on a flexible planar circuit substrate comprising:
   a conductor configuration on a first substrate surface and a plurality of electronic components on an opposite, second substrate surface, wherein the components have component contacts, which are electrically connected selectively by way of vias in the circuit substrate and the conductor configuration,
   wherein the circuit substrate is a thermoplastic polymer which allows the component contacts to be melted or thermally pressed into the second substrate surface in the region of the vias,
   the electronic module further comprising a thermoplastic protective film encapsulating at least one of the components, at least on the second substrate surface.

2. The electronic module according to claim 1, wherein the conductor configuration is formed from a first metallization layer and the vias are formed from a second metallization layer.

3. The electronic module according to claim 1, wherein the vias have a metallization deposited in bores of the circuit substrate.

4. The electronic module according to claim 3, wherein the deposited metallization is galvanically reinforced.

5. The electronic module according to claim 3, wherein the vias comprise at least one metal from the group of copper, gold, titanium, tungsten, palladium, chromium, and nickel.

6. The electronic module according to claim 1, wherein the thermoplastic polymer or one thermoplastic polymer comprises at least one material from the group of liquid-crystal polymer or LCP; polyether ether ketone, or PEEK; polyetherimide or PEI.

7. The electronic module according to claim 1, wherein the circuit substrate has a thickness in a range between 10 μm and 500 μm, in particular between 10 μm and 100 μm.

8. The electronic module according to claim 1, formed as an implantable electromedical implant or module thereof.

9. A method for producing an electronic module according to claim 1, comprising the following steps:
   providing the flexible planar circuit substrate comprising a thermoplastic polymer, producing the conductor configuration on the first substrate surface, producing a bore pattern in accordance with a geometry of the conductor configuration, heating the components that are to be placed on the second substrate surface, placing the components, aligned with the bore pattern in the circuit substrate, on the second substrate surface with a predetermined contact pressure and hereby fusing or thermally pressing the component contacts into the second substrate surface in a region of the bore pattern, depositing metal selectively into the bore pattern and in the surroundings of bores from the first substrate surface in order to produce the vias, and laminating a thermoplastic protective film on at least a part or parts of the second substrate surface.

10. The method according to claim 9, wherein the components are heated to a placement temperature in the range between 100° C. and 400° C., in particular between 250° C. and 350° C., and/or the predetermined contact pressure lies in a range between 0.05 N and 50 N, in particular between 0.1 N and 30 N.

11. The method according to claim 9, wherein the depositing of metal in the bore pattern is performed following the fusing or thermally pressing of the components by means of an electrochemical or physical thin-film process including CVD or PVD.

12. The method according to claim 11, wherein, following the metal deposition, a galvanic reinforcement of a deposited thin film is performed.

13. The method according to claim 9, wherein the protective film is laminated on at a temperature in the range between 100° C. and 400° C., in particular between 250° C. and 350° C. and/or the predetermined contact pressure lies in a range between 0.05 N and 50 N, in particular between 0.1 N and 30 N.

14. The electronic module according to claim 1, wherein the components adhere flush without gaps to the second substrate surface.

* * * * *